United States Patent [19]

Zakko

[11] Patent Number: 4,902,276
[45] Date of Patent: Feb. 20, 1990

[54] APPARATUS AND METHOD FOR REMOVING OBSTRUCTIONS IN BODILY ORGANS OR CAVITIES

[75] Inventor: Salam F. Zakko, Farmington, Conn.

[73] Assignee: The Regents of the University of California, Berkeley, Calif.

[21] Appl. No.: 180,099

[22] Filed: Apr. 11, 1988

Related U.S. Application Data

[63] Continuation-in-part of Ser. No. 871,775, Jun. 9, 1986, abandoned.

[51] Int. Cl.$^4$ .......................... A61M 1/00; A61M 5/00
[52] U.S. Cl. .......................................... 604/28; 604/31; 604/43; 604/66; 604/317
[58] Field of Search ................................ 604/27-34, 604/43, 21, 48-51, 65-67, 118-120, 151, 153, 246, 284, 317; 128/328, 748, 750, DIG. 12, DIG. 13; 417/2, 38, 44, 279, 302

[56] References Cited

U.S. PATENT DOCUMENTS

| | | | |
|---|---|---|---|
| Re. 31,873 | 4/1985 | Howes | 604/21 |
| 2,908,273 | 10/1959 | Huston | 604/151 |
| 3,316,910 | 5/1967 | Davis | 128/328 |
| 3,329,147 | 6/1967 | Barron | 128/230 |
| 3,410,268 | 11/1968 | Leucci | 128/227 |
| 3,433,227 | 3/1969 | Kettenbach | 604/43 |
| 3,520,298 | 7/1970 | Lange | 604/29 |
| 3,545,438 | 12/1970 | De Vries | 604/29 |
| 3,788,305 | 1/1974 | Schreiber | 604/35 |
| 3,900,022 | 8/1975 | Widran | 604/31 |
| 4,024,866 | 5/1977 | Wallach | 604/31 |
| 4,117,843 | 10/1978 | Banko | 604/31 |
| 4,217,911 | 8/1980 | Layton | 604/118 |
| 4,261,360 | 4/1981 | Perez | 604/31 |
| 4,412,917 | 11/1983 | Ahjopalo | 604/29 |
| 4,466,804 | 8/1984 | Hino | 604/31 |
| 4,573,966 | 3/1986 | Weikl et al. | 604/101 |
| 4,586,920 | 5/1986 | Peabody | 604/31 |
| 4,626,239 | 12/1986 | Ardizzone | 604/31 |
| 4,655,744 | 4/1987 | Thistle et al. | 604/28 |
| 4,696,668 | 9/1987 | Wilcox | 604/28 |
| 4,755,167 | 7/1988 | Thistle et al. | 604/28 |
| 4,758,596 | 7/1988 | Thistle et al. | 514/722 |

FOREIGN PATENT DOCUMENTS

| | | |
|---|---|---|
| 297208 | 3/1972 | Austria . |
| 2946444 | 5/1981 | Fed. Rep. of Germany . |
| 2230283 | 1/1984 | Fed. Rep. of Germany . |
| 8700759 | 2/1987 | PCT Int'l Appl. . |
| 159951 | 4/1964 | U.S.S.R. ............... 128/328 |

OTHER PUBLICATIONS

Mack et al., "Percutaneous Transhepatic Dissolution of Common Bile Duct Stones"; Surgery 1981; 90:584-587.
Allen et al., "Rapid Dissolution of Gallstones by Methyl Tert-Butyl Ether", N. Eng. J. Med., 312, 4, 217 (Jan. 24, 1985).
Shortsleeve et al., "Monooctanoin Dissolution of Gallstones via a Cholecystostomy Tube", Radiology, 153, 2, 547 (1984).
Teplick et al., "Monooctanoin Perfusion for In Vivo Dissolution of Biliary Stones", Radiology, 153, 2, 379 (1984).
Thistle et al., "Dissolution of Cholesterol Gallbladder Stones (CGS) Using Methyl Tert-Butyl Ether", Gastroenterology, No. 5, Pt. 2, 1775 (May, 1986).
Walker, "The Removal of Gallstones by Ether Solution", The Lancet, 874 (Apr. 18, 1891).

Primary Examiner—Stephen C. Pellegrino
Attorney, Agent, or Firm—Brown, Martin, Haller & McClain

[57] ABSTRACT

A fully automatic organ pressure sensitive apparatus for dislodging and removing obstructions in bodily cavities or organs by both delivering and removing fluid thereto, operable by high rate continuous or intermittent infusion of fluid solvent over a set pressure range to effect rapid dissolution and removal of the obstruction without complications to the patient. By continuous feedback monitoring of fluid pressure in the bodily organ or cavity of interest, the apparatus can constantly vary infusion and aspiration rates to maintain the set passages range. If the pressure persists above or below the set range, the apparatus activates a safety feature leading to a period of maximal aspiration and cessation of infusion, followed by cessation of solvent transfer and triggering of an alarm to alert the operator.

35 Claims, 5 Drawing Sheets

APPARATUS AND METHOD FOR REMOVING OBSTRUCTIONS IN BODILY ORGANS OR CAVITIES

This application is a continuation-in-part of copending application Ser. No. 06/871,775, filed June 9, 1986 now abandoned.

BACKGROUND OF THE INVENTION

For most individuals who suffer from gallstones, the treatment of choice is to have a cholecystectomy, or surgical removal of the gallbladder. Each year 500,000 such operations are done in the United States alone. Recently, because of the cost and possible side effects associated with this surgery, methods have been developed for chemically removing gallstones in situ. Generally, this procedure involves inserting a catheter into the gallbladder followed by infusing a chemical solvent capable of dissolving the gallstone. The procedure thus avoids the need for and attendant risk of surgery.

A variety of chemical solvents have been tried and found to exhibit varying efficiencies of gallstone dissolution, depending on the chemical nature of the gallstone. Gallstones are generally composed of cholesterol or calcium salts, particularly calcium bilirubinate and calcium carbonate. Lipid solvents are effective at dissolving cholesterol gallstones, whereas these solvents have little or no solubilizing effect on gallstones composed of calcium salts. Thus, diethyl ether readily dissolves cholesterol gallstones, and other solvents such as mono-octanoin, and octadiol (glyceryl-1-octyl ether) also have good solubilizing properties. Unfortunately, few if any solvents are satisfactory for dissolving calcium gallstones. The invention herein will therefore find principal utility in cholesterol gallstone removal. It has been recognized that methyl tert-butyl ether (MTBE), a solvent hithertofore used primarily as a gasoline additive and a chromatographic solvent media, has outstanding cholesterol gallstone dissolving properties. Moreover, the solvent rapidly dissolves the gallstones without damaging the mucosa of the gallbladder.

The effectiveness of solvents has led to considerable activity focused on developing apparatus and methods for delivering MTBE and similar solvents to patients suffering from gallstones in ways to most rapidly and effectively solubilize gallstones without the complications arising from introducing such solvents into the body. (For brevity herein, the description will be with respect to use of MTBE as a solvent. It will be recognized, however, that this invention will be applicable to a number of different solvents.)

Physicians currently treat cholesterol gallstones by infusing MTBE into the gallbladder through a percutaneously positioned catheter through which MTBE is manually passed using glass syringes [Walker, *Lancet* 1, 874 (1891); Shortsleeve, *Radiology*, 153, 547 (1984); and Teplick, *Radiology*, 153, 379 (1984)]. Additionally, physicians have have available fixed volume syringe pumps, such as described in U.S. Pat. No. 4,655,744 to Thistle et al. to infuse and aspirate MTBE. There are several complications associated with either the manual infusion or the fixed volume pumpassisted infusion procedure.

When MTBE is delivered manually via glass syringes or with the aid of a fixed volume-cycle pump, spontaneous gallbladder contraction or over filling of the gallbladder cannot be detected or controlled. Consequently, MTBE periodically empties into the duodenum, producing duodenal mucosal injury, which in turn produces nausea, vomiting, duodenal erosions and accompanying pain of sufficient intensity to necessitate frequent administration of analgesics. In addition, when in the duodenum MTBE can be absorbed into the blood stream, which in turn may result in somnolence or hemolysis and concomitantly the presence of the intense and irritating MTBE odor in the patient's breath.

Other problems associated with the manual or pumpassisted syringe method involve inefficient removal of insoluble gallstone particles which constitute varying percentages of cholesterol gallstones. Such particles are often left behind in the gallbladder after MTBE dissolves the cholesterol portion in procedures involving syringes or syringe pumps. These particles often serve as the nidus for new gallstone formation. Additionally, both procedures are time consuming, laborious and require individuals that are highly skilled in their use. Consequently, the procedures are expensive because of the attendant costs associated with having a highly skilled staff of professional people to perform the procedure for prolonged times, often 12 hours or more.

It is obvious that delivering MTBE to a patient requires the utmost care to avoid releasing the solvent into the patient's bodily fluids or outside the area of treatment. THus a key consideration in developing devices used in the chemical therapy of gallstone dissolution is ensuring the controlled delivery and removal of the solvent used to dissolve the gallstones. Considering that studies have shown that solvents such as MTBE are injurious if they pass into the intestine where they get absorbed, there is a critical need for devices that ensure that such chemicals will not be released during chemical therapy for gallstone removal. At the same time such devices must be able to maintain high solvent circulation rates into the gallbladder to create the necessary turbulence that will enhance dissolution and aid in evacuating the insoluble residue.

Also, because of the need to ensure containment of solvents, in addition to the safety features described above a suitable device should be "user friendly" and not require the presence of highly skilled technicians to run the device. Further, for the same reasons, it should be easily maintainable.

With a little reflection, it becomes apparent that there are considerable hurdles to surmount if one is develop a device that has the features described above. For instance, it must be "intelligent" and capable of sensing instantaneous changes in gallbladder pressure brought about by gallbladder contractions or by infusing the solvent, and rapidly relay this information to controlling feedback circuits. This is a crucial feature for such a device. If a gallstone should in some way prevent the necessary circulation of the solvent through the gallbladder, a critical pressure will build up, possibly rupturing the organ or causing leakage of the solvent from the gallbladder through the cystic duct into the common duct and intestine. Thus the device must be "intelligent" in the sense that it senses gallbladder pressure changes over a predefined range and reacts fast enough to keep the pressure in that range, shutting down if the pressure persists outside the range. Moreover, it would be desirable to have a device that not only is capable of shutting down, but actually can flush out any debris causing the blockage, and resume normal operation should the debris be removed.

SUMMARY OF THE INVENTION

The invention herein comprises an apparatus and a method for its use which are for therapeutic treatment of obstructions in bodily organs by high rate solvent circulation, particularly for gallbladder or common bile duct stones. The apparatus has the desirable feature of continuous high rate infusion and aspiration while preventing solvent leakage from the bodily organ being treated. The apparatus comprises a forward or reverse acting solvent delivery means that is linked via a pressure transducer to a feedback controller circuit.

The apparatus is preset to perfuse within a set pressure range. Continuous feedback of true intraluminal organ pressure to a controller circuit via the transducer controls the rate and the net direction of solvent delivery by the apparatus and is determinative of whether the apparatus acts in the forward or reverse mode. Over this range the solvent is constantly passed from a reservoir into the gallbladder, and from the gallbladder it is aspirated to a suitable receptacle. Delivery and removal of the solvent is at a rate sufficient to effect gallstone dissolution and fragmentation, agitation and aspiration of insoluble fragments. Should there be an increase in pressure, a feedback loop switched the device into a high pressure mode, thereby diverting the solvent away from the gallbladder. If after a predetermined period of time the pressure sensing transducer readings from the gallbladder indicate a return to normal operating pressure range, the device automatically reinitiates the normal infusion and aspiration (perfusion) mode.

An additional feature of the invention is a self purging mechanism. After a preset interval, if the pressure does not decrease, the device enters a reverse mode to purge the aspiration port of the catheter, whereby fluid is aspirated backward through the infusion port and infused through the aspiration port to purge for discrete short intervals, during which time the pressure in the organ is continuously monitored. Once the blockage is removed by this "self-purging" action, the pressure transducer again indicates normal operating pressure, and the device resumes action in the normal pressure mode. However, should the obstruction not be removable after a predetermined number of purge cycles, an alarm circuit is activated, so notifying the user. A further feature of the invention is that it is able to distinguish clinically significant pressure changes occurring within the gallbladder which leads to emptying of gallbladder contents into the duodenum from those clinically insignificant changes arising as a result of coughing, laughing or like behavior. This feature prevents needless changes of operating modes.

DETAILED DESCRIPTION OF THE INVENTION

The invention described herein is suitably employed for delivering fluids (solvents) to organs for removing obstructions contained therein. It will be appreciated at the outset that, while the subject invention described below details the invention regarding the removal of gallstones from the gallbladder, the invention can be used to remove a variety of obstructions from bodily cavities or organs other than the gallbladder, and thus should not be construed as being narrowly limited to the treatment of gallstones. Indeed, it will become readily apparent that the device is easily adapted to removing obstructions from organs or bodily cavities in general.

The invention described herein is an organ pressure sensitive apparatus having a solvent delivery means in constant communication with a controller circuit via one or more pressure transducers that monitor the intra-organ pressure. The apparatus functions over a preset pressure range delivering fluid to the gallbladder, causing the fluid to contact and dissolve the gallstones, and withdrawing fluid from the gallbladder, thereby accomplishing the removal of dissolved or fragmented gallstones. The rate of solvent delivery and removal can be adjusted to create the necessary turbulence to dissolve or fragment gallstones. If the pressure exceeds that of the normal operating range, the apparatus diverts solvent from the organ, thereby preventing leakage of the solvent from the site of treatment. Further, above the normal operating pressure range, the apparatus can be programmed to be "self-purging". This may be desirable in the instance when the obstruction is only partially dissolvable, causing blockage of the solvent removal or aspiration means. At pressures below the normal operating pressure range, the rate of aspiration is decreased while infusion continues, thereby reestablishing normal operating pressure.

A key consideration with regard to the organ pressuresensitive aspects of the system is the realization that leakage of solvent from the gallbladder occurs when the intraluminal pressure exceeds that in the cystic duct, common bile duct or ampula (whichever is selected for the procedure in a particular patient) and that neither the gallbladder volume per se nor the flow rate of solvent per se are intimately involved. This in turn leads to recognition that critical leakage pressure from the gallbladder differs from patient to patient, and that leakage is a function not only of solvent delivery but natural gallbladder contractions or extrinsic pressure to the gallbladder. The subject invention takes into account those pressure changes that are of sufficient duration or strength to affect solvent leakage.

Figure 1:
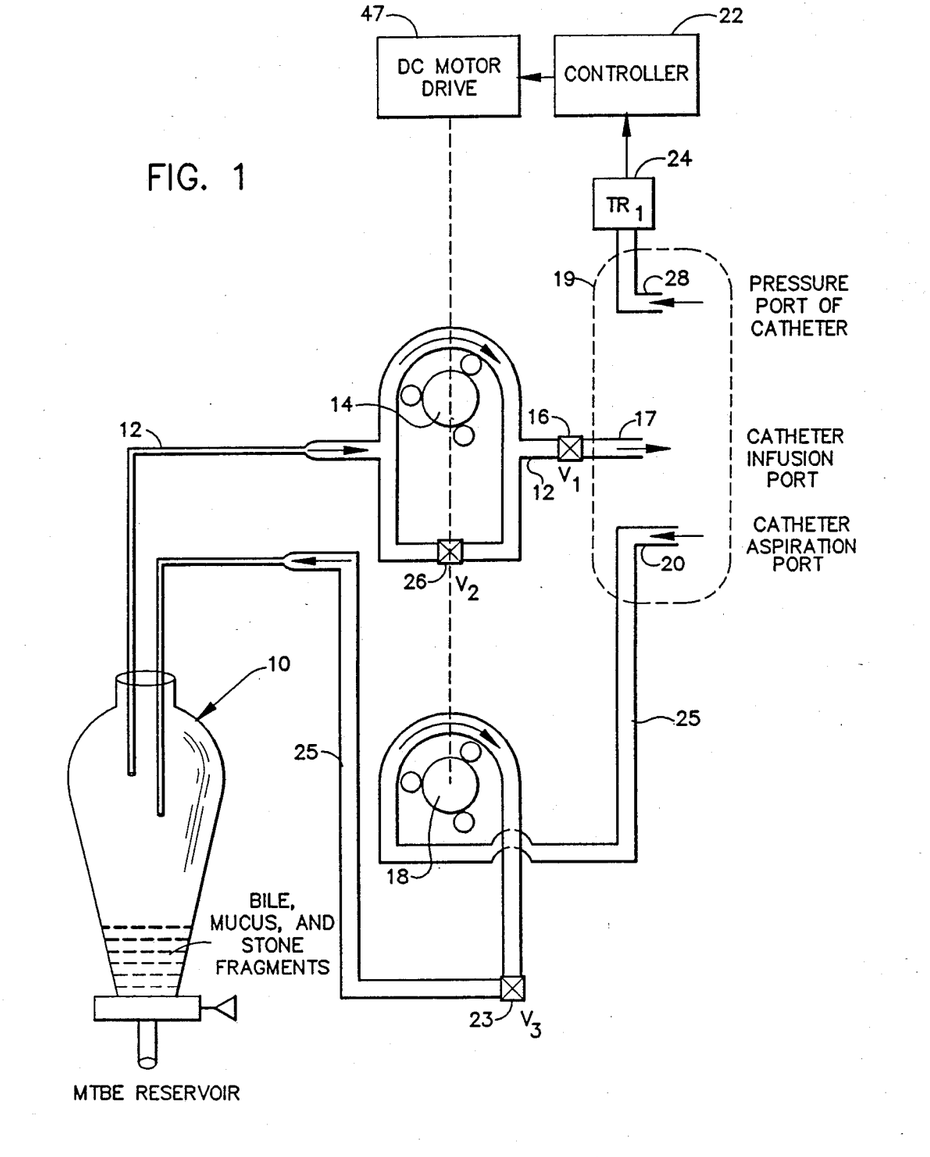
FIG. 1 is a schematic diagram of an apparatus suitable for delivering solvent to a gallbladder and for removing the solvent containing dissolved or fragmented gallbladder stones.

FIG. 1 shows an exemplary apparatus for removing gallstones. Reservoir 10 contains a solvent that is a chemical suitable for dissolving gallstones. Should the gallstone be composed of cholesterol, a variety of solvents would be efficacious. Particularly effective is methyl tert-butyl ether (MTBE). The latter has been shown to readily dissolve cholesterol stones rapidly both in vitro and in vivo. At normal operating pressures, the solvent moves via a conduit 12 from the reservoir 10 by aid of a first pump 14. The fluid then moves through a valve 16 and from the valve through infusion port 17 in a catheter 19 into the gallbladder. During this operation valve 26 is closed to prevent solvent return to reservoir. The solvent is delivered at a predetermined effective rate for gallstone dissolution thereby providing solvent turbulence and contact with the gallstones for a period of time sufficient for effective gallstone dissolution or fragmentation and fragment removal.

Simultaneously with the delivery of MTBE to the gallbladder, a second pump 18 aspirates the fluid from the gallbladder now containing dissolved gallstones and debris. This material passes out of the gallbladder via an aspiration port 20 in the catheter. The fluid moves from the catheter, passing through a valve 23, and from there it is deposited in a receiver reservoir. Either reservoir 10 used as the source of the solvent or a separate reservoir is suitable for this purpose. FIG. 1 shows the same reservoir 10 being utilized as both the source of fluid passed to the gallbladder and as the receiver of aspirated fluid therefrom. It is worth noting that if the same reservoir is used, gallbladder stone fragments, bile, mucous and the like removed from the gallbladder are heavier than the solvent, MTBE, and therefore settle to the bottom of the reservoir and do not hinder continued withdrawal of essentially pure fluid from the reservoir to effect further stone dissolution.

The pumps 14 and 18 are controlled by a controller circuit 22. The controller circuit 22 in turn receives pressure readings from the transducer 24 causing the controller circuit 22 to open or close flow valves 16, 23 and 26 to inhibit infusion or aspiration as necessary to control organ pressure depending on whether the transducer 24 indicates that the pressure in the gallbladder is within, above or below the normal operating pressure range. The transducer in turn senses the gallbladder fluid pressure by communication through port 28 of the catheter 19.

At the preset normal operating pressure, first pump 14 delivers fluid from reservoir 10 through tube 12 and valve 16 to the gallbladder. Simultaneously, and at a slightly slower rate, second pump 18 aspirates the fluid from the gallbladder through catheter aspiration port 20. Fluid passes through the valve 23 and thence through conduit 25 to a reservoir.

Conduit 12, catheter 19 and conduit 25 form a fluid circuit connecting the source reservoir 10 with the bodily organ or cavity into which the catheter is inserted and then to the receiving reservoir (which as noted may also be reservoir 10). The pumps 14 and 18 are in the circuit, in conduits 12 and 25 respectively. (For the purpose of description herein, the "forward" fluid flow direction will be defined as flow in the direction of the arrows in FIGS. 1 and 6, and "reverse" flow will be flow in the direction opposite the arrows.)

The controller 22 is programmed to respond to pressures that exceed or are below that of the normal operating pressure range. Above the normal operating pressure range ("high pressure mode"), the controller 22 shuts down valve 16 and simultaneously opens valve 26. This provides a path for diverting the incoming fluid away from the gallbladder. At that time valve 23 is open to continue gallbladder emptying to return the pressure to the normal operating range. If the pressure in the gallbladder does not return to the normal operating pressure setting within a preset time, for example a few seconds, then the controller 22 can be programmed to instruct the pumps to reverse the direction of fluid movement, and simultaneously valves 23 and 26 are closed. The controller unit is programmed to close valve 23 after a slight delay so that a small amount of fluid, approximately 1 ml, can pass through the valve before it is shut. Valve 16 is opened to provide a path for fluid to be reverse aspirated from the gallbladder in this "selfpurging" mode. This mode essentially causes a small amount of fluid to be pumped in through the aspiration port 20 of the catheter 19 to clear it from obstructions while aspiration is effected by pump 14 through valve 16. The fluid which is pumped into the gallbladder passes from the reservoir 10 through valve 23, prior to valve 23 closing in response to high pressure present in the gallbladder. Generally this will consist of about 1 ml of fluid passing through valve 23 before it shuts. This mode of operation continues for a brief period of time, and then the controller unit 22 instructs the machine to resume normal operation should the obstruction be removed and the pressure transducer 24 indicate reestablishment of normal operating pressure range. If the transducer continues to indicate pressures present in the gallbladder above the normal operating pressure, the controller unit 22 again instructs the pumping apparatus to purge the system. If, after several "self purging" cycles, the obstruction is still not removed, the controller unit 22 then shuts down the system and activates an alarm circuit 34 notifying the user of a potentially dangerous condition.

Figure 2:
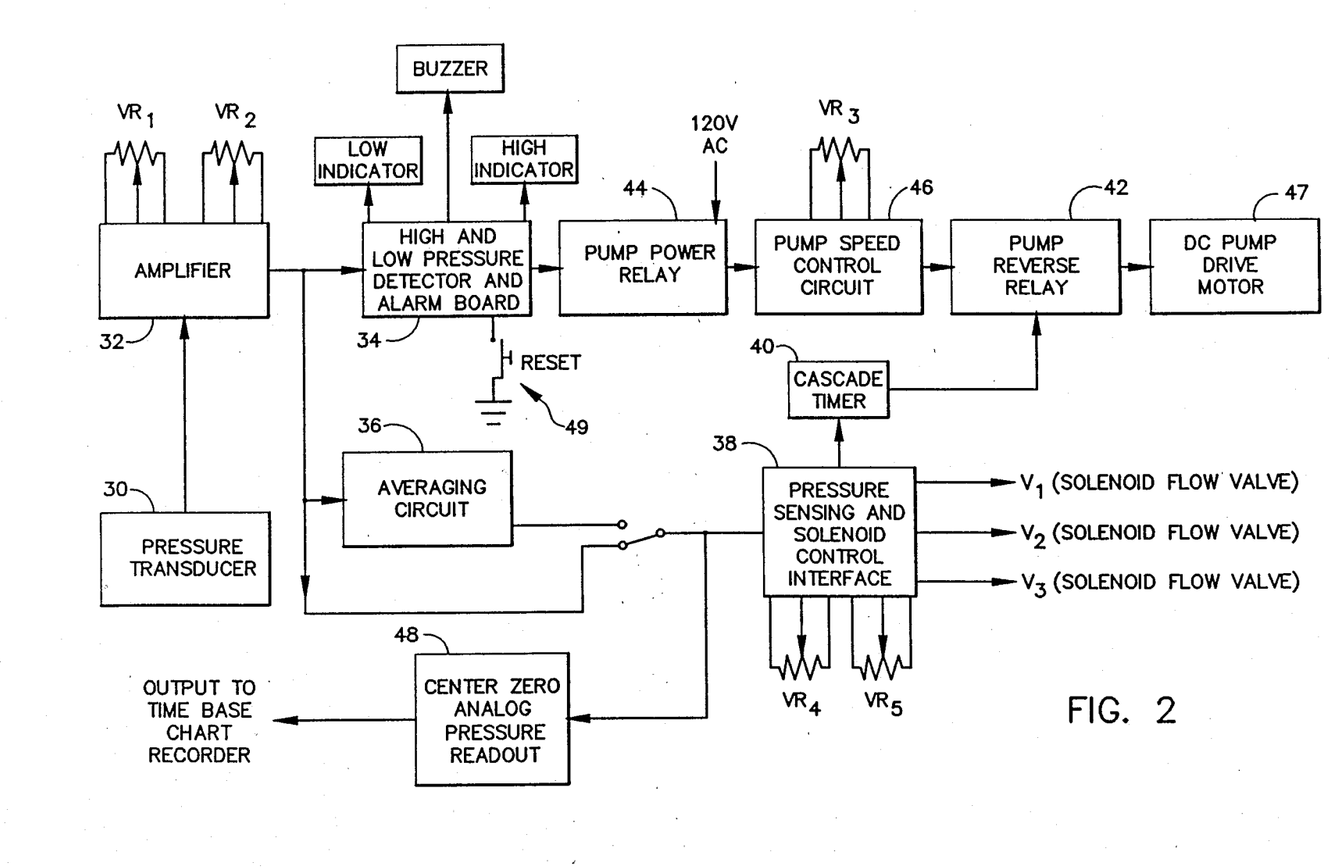
FIG. 2 is a schematic diagram of a controller circuit that regulates the pump units shown in FIG. 1, as well as other features of the apparatus.
Figure 3:
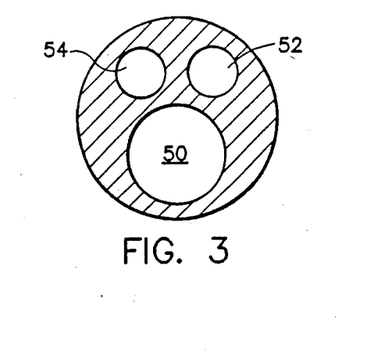
FIGS. 3, 4 and 5 show features of a three-lumen catheter, FIG. 3 being a sectional view taken on line 3—3 of FIG. 4.

FIG. 2 illustrates a representative controller unit 22. The controller circuit 22 instructs the pumps 14 and 18 to deliver or aspirate fluid from the gallbladder. Thus, a circuit will typically have a pressure transducer 30; an example of a suitable transducer is a Statham gold pressure transducer P23ID. The pressure transducer 30 relays information to an amplification device 32 which amplifies the signal and transmits it to a high and low pressure alarm circuit 34, then either directly or through the averaging circuit 36 to a pressure-sensing circuit 38 that reads preset low and high pressure values and which is connected to the valves 16, 23 and 26. The latter valves are typically solenoid flow valvesor tube compression valves. The averaging circuit 36 can be switched in if desired to discriminate between pressure changes in the gallbladder arising from fluid build-up due to obstructions or from hyperventilating, laughing or like activities. Thus the averaging circuit essentially screens out artificially high or low pressure peaks which in fact do not lead to gallbladder emptying.

The pressure sensing circuit 38 is connected to a cascade timer 40, which in turn is connected to a pump reverse relay circuit 42. Thus, when gallbladder pressure exceeds that of the normal operating pressure range and the obstruction is not removed within a predetermined period, the cascade timer 40 activates the pump reverse relay 42. The latter circuit is responsible for "self-purging" the system. Should high pressure persist after several brief "self purging" cycles, then the alarm circuit 34 is activated, causing an initial period of aspiration in the reverse mode (with valves 16 and 23 open and valve 26 closed), then stopping the pumping system by shutting off its power supply and the triggering of a visual, audible or other alarm notifying the user. Note that at any time during the pump reverse cycle, should the pressure return to within the normal pressure range, the apparatus resumes normal operation.

It will be further noted as shown in FIG. 2 that a pump power relay circuit 44 and a pump speed control circuit 46 are also interactive with the whole system. The pump speed control circuit 46 derives power through the pump power relay 44, which in turn is controlled by the alarm circuit 34. The pump motor derives its power supply from the pump power relay 44. Any time an alarm condition exists, this relay shuts off power to the pump, stopping it from pumping. The pump speed control circuit 46 has a manual adjustment capability through which the operator can set the desired perfusion rate for that specific situation. An analogue pressure read-out 48 is provided for the operator to assess effective operation and to refer to during calibration. Alternatively, or in addition, the output can be fed to a video display terminal driven by appropriate software to provide the operator with an intermittent or continuous display of system operating mode, pressure, etc., and may be integrated with the indicators and alarm of alarm circuit 34.

Note that if desired one or more appropriate microprocessors can replace either or both of the relay circuits 42 and 44 or components 36, 38, 40.

Figure 6:
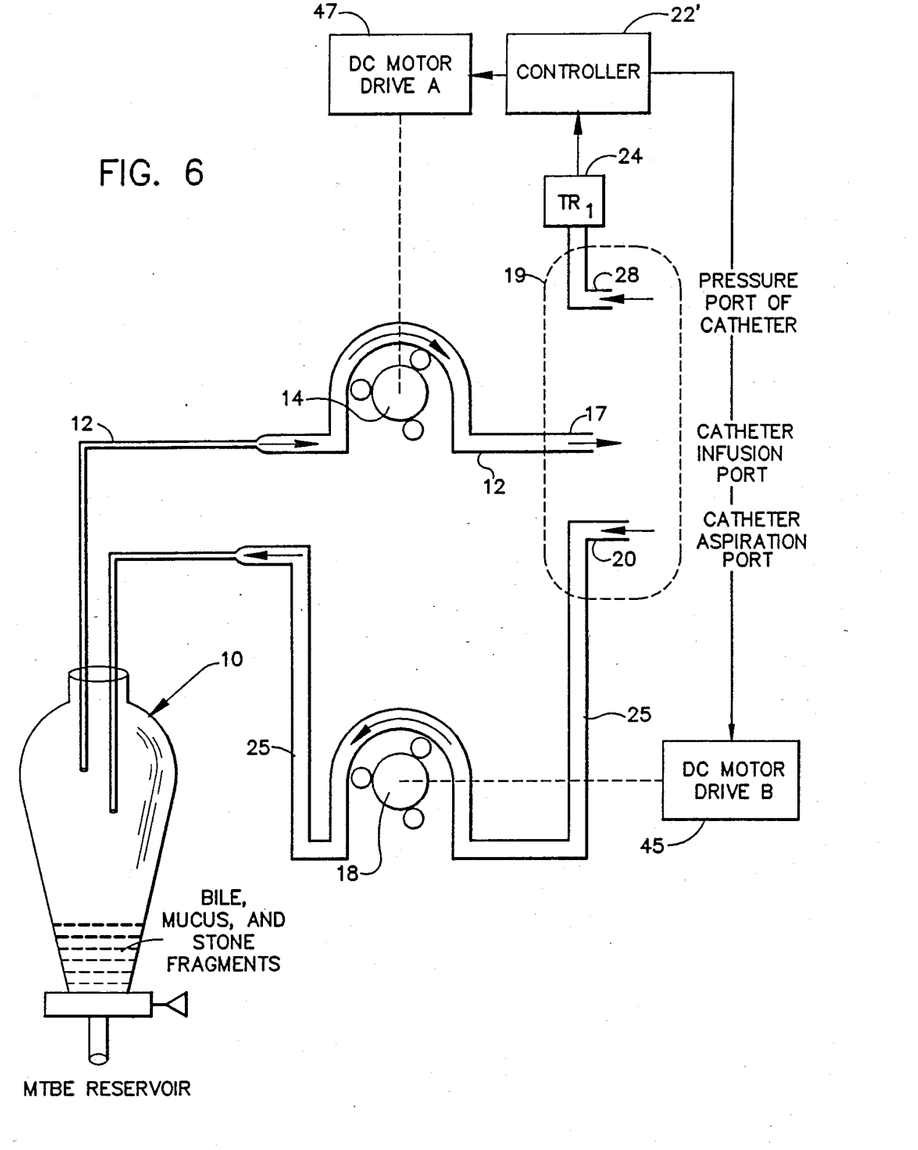
FIG. 6 is a schematic diagram of another embodiment of the apparatus.

FIG. 6 illustrates an alternative embodiment of the apparatus, which eliminates the valves by having separate control of the two pumps 14 and 18. Each pump motor has its own DC drive 47 and 45 respectively. Both drives are controlled by controller 22', which has an appropriate microprocessor to control the speed of each motor (and thus the flow rate of each pump) in response to the pressure signals from transducer 24. Thus instead of opening and closing valves to effect the proper infusion, aspiration or purging, the controller 22' regulates each pump's flow rate and direction of flow.

This embodiment has the advantage that all fluid conduits (tubing, catheter, reservoir) can be made of easily replacable material. Thus each patient can be treated using a system in which all wettable surfaces are limited in use solely to that one patient and one treating session.

There are several features of the apparatus that enhance its performance. The pumps preferred in the subject invention are peristaltic pumps. This type of pump offers several advantages such as the replacable wettable surfaces mentioned above, which in addition to their individual sterility will be particularly advantageous in those instances where the solvent being used to dissolve the obstruction is at all corrosive. Moreover, peristaltic pumps are resistant to clogging, in contrast to standard syringe type pumps. However, it should be noted that syringe pumps are similarly employable in the subject invention in those instances where the fluid used to dissolve and remove the obstruction is a solvent, provided that the syringe pumps are constructed of suitable material, preferably polytetrafluoroethylene (PTFE) or glass. Syringe pumps made of plastic are not preferred in instances where the solvents used are incompatible with the plastic composition of the syringe. An additional disadvantage associated with the use of syringe pumps that is not present in peristaltic pumps is that in those instance where a solvent is being utilized, evaporation of the solvent from between the plunger and the body can cause deposits in the body of the syringe, causing it to "freeze" and thus interrupt delivery of the fluid to the organ being treated. Lastly, peristaltic pumps are capable of much greater fluid circulation rates than a syringe pump. This is advantageous in certain instances where the obstruction to be removed, such as a gallstone, requires turbulent flow rates across the surface of the gallstone to accelerate the dissolution process.

A predetermined normal operating pressure range is programmed into the controller circuit 22. Should the pressure in the gallbladder exceed normal operating pressure, the action of the controller circuit 22 prevents leakage of solvent from the gallbladder through the cystic duct into the common duct, as well as into the intestine or around the entry site of the catheter. Also, because the controller circuit "sees" true gallbladder pressure, it readily adjusts to decrease as well as increase pressure by adjusting the net delivery rate of the solvent to the gallbladder. For example, should the pressure fall below the normal operating pressure range, the controller circuit 22 ceases or slows down the rate of aspiration of solvent, and simultaneously continues infusing solvent to reestablish normal operating pressure.

The pressure sensitive alarm circuit 34 is constantly monitoring system operation and gallbladder pressure. If gallbladder pressure cannot be brought into the normal operating pressure range by the action of the controller circuit 22 in a specified period of time, it will revert to a period of maximal aspiration, then shut down the pumping system and sound an alarm drawing the attention of the operator. The operator, after correcting the problem, can resume normal operation by activating the reset button 49.

The apparatus is completely automatic and is operable without any significant operator input. Moreover, it is readily converted to a completely closed circuit system in those instances where the therapeutic fluid is combustible. This feature is required for particularly combustible solvents.

Any of a number of types of tubing is suitably used with the pumps of the subject apparatus. However, we have found that tubing composed of "Tygon Special Formulation F-4040A" (a vinyl material) or "Nalgene" (a polyurethane) is particularly compatible with solvents such as methyl tertbutyl ether. Moreover, tubing with a large internal diameter is favored for use with peristaltic pumps, enabling a high volume per revolution ratio to be obtained, thereby permitting a low revolution per minute rate to be utilized, hence minimizing torque build-up when a switch over to the high pressure mode leads to pump motor reverse.

As discussed above, the subject apparatus can be utilized for removing obstructions in a variety of organs. However, in the instance where it is used to remove gallstones from gallbladders, perfusion rates of about 50 ml/min to 300 ml/min are generally more effective. This is readily accomplished by manually adjusting the pump speed control circuit 46.

Figures 4, 5:
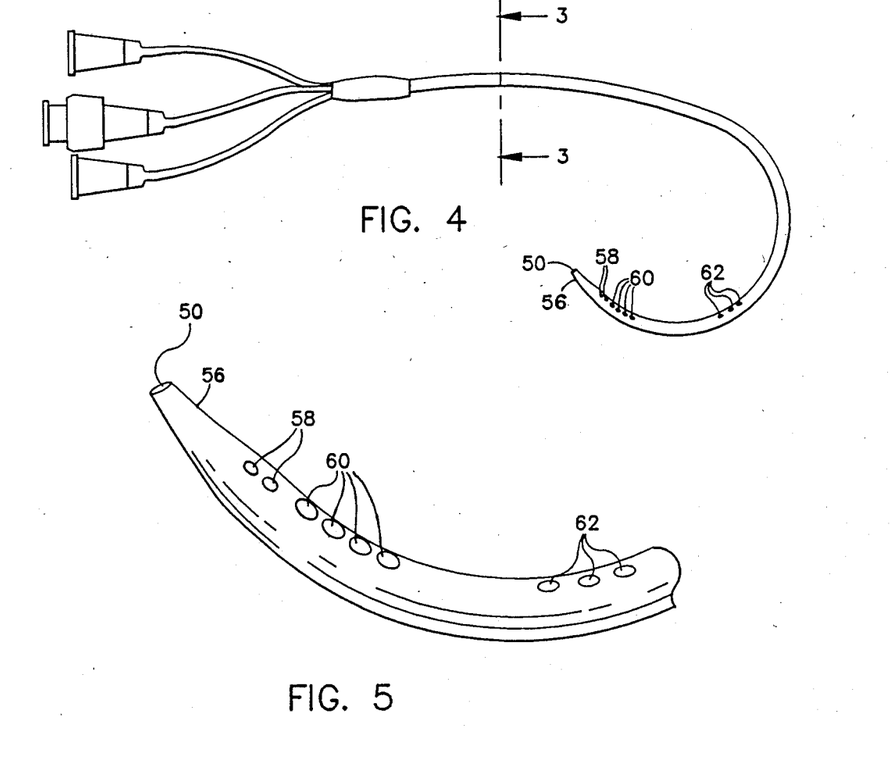
Figure 7:
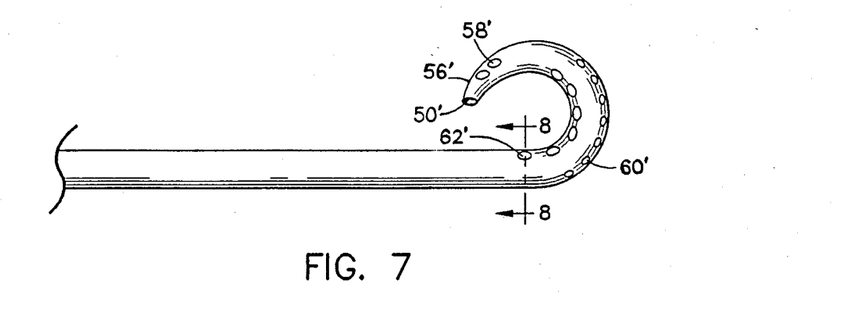
FIGS. 7 and 8 show features of another suitable three-lumen catheter, with FIG. 8 being a sectional view taken on line 8—8 of FIG. 7.
Figure 8:
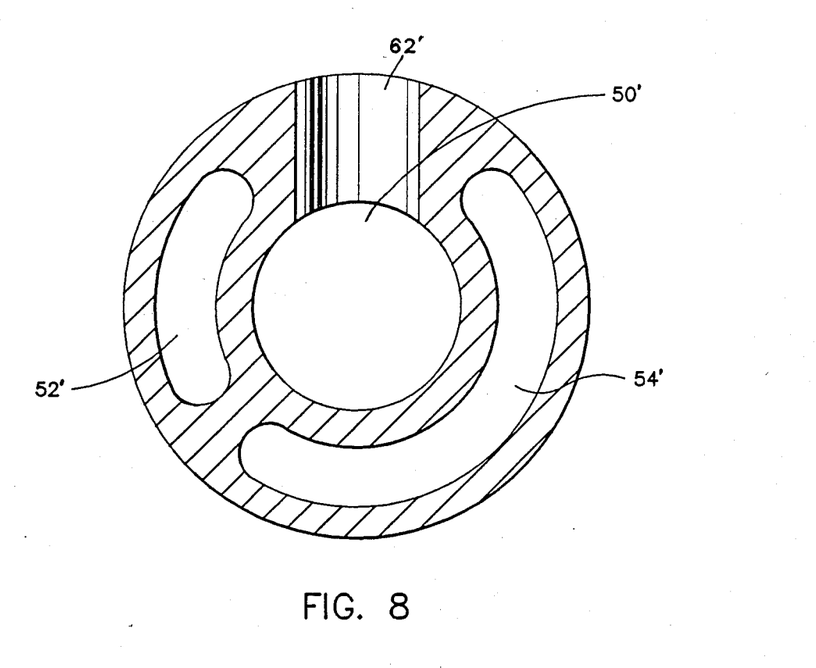

A variety of catheters usable to deliver and aspirate the fluid can be suitably employed. However, three-lumen catheters as shown in FIGS. 3-5 and 7-8 are favored since pressure measurements as well as perfusion and aspiration of the fluid can all be carried out simultaneously. A suitable three-lumen catheter should have an outside diameter not larger than can be readily employed for the surgical insertion of the catheter into the gallbladder, and should have an aspiration lumen 50, a pressure sensing lumen 52 and an infusion lumen 54. To effectively remove dissolved gallstone debris and the like, it is preferred that the aspiration lumen be larger in diameter than either of the two other lumens Of course size and number of the entry/exit ports at the distal terminal of each lumen will be appropriate to the lumen cross-sectional area. FIGS. 4 and 5 further show another feature of one embodiment of the catheter. It has an elongated tapered tip 56, holes in the tip 58 and 60 that provide a means for fluid communication with the pressure sensing lumen and the infusion lumen, respectively. In addition there are openings 62 in the wall of the catheter that provide a means for communication of fluid between the gallbladder and the aspiration lumen. Note that the number of openings is not invariant, depending on the number of gallstones present in the gallbladder, as well as the desirable therapeutic need to effect rapid treatment. The distal end of the catheter is preferably curved into a pigtail shape as shown in FIG. 7 to aid in its being retained and positioned in the organ.

The system should not be construed as being limited to a three-lumen catheter. A variety of catheters of different lumens will perform satisfactorily provided that the system is modified to accommodate such catheters, such modifications being well known to those skilled in the art.

It will be appreciated by those skilled in the art that there are numerous modifications in the eLectrical circuitry, and the overall interconnecting features of the invention that will achieve the efficacious removal of obstructions in particular organs. For instance, while the automatic "self purging" feature of the apparatus is desirable, a device without this feature will perform adequately. Moreover, it should be further noted that, while the invention has been described as applicable to the removal of gallstones from gallbladders, its use should not be so narrowly construed. Thus, it is the intent herein to present an invention that is generally applicable for the removal of obstructions from a variety of organs by dissolving and dislodging the obstruction using solvents.

I claim:

1. Apparatus for removal of a soluble obstruction in a bodily organ or cavity, comprising:
   source reservoir means for containing a fluid capable of dissolving said obstruction;
   first and second fluid conduits attached to and forming a fluid circuit with said reservoir means and said organ or cavity and providing fluid communication between said reservoir means and said organ or cavity;
   pump means associated with each of said conduits to move said fluid in said conduits around said circuit;
   means for detecting and measuring fluid pressure in said organ or cavity, said means adapted to classify said pressure as high, normal or low according to predetermined physiological criteria; and
   means operatively connecting said means for detecting and measuring pressure and each of said pump means and responsive to said organ or cavity fluid pressure to cause said pump means to maintain forward fluid flow at low and normal pressure and to decrease or reverse fluid flow at high pressure.

2. Apparatus as in claim 1 wherein said responsive means comprises:
   controller means to operate said pumps;
   a first valve situated in said first fluid conduit and opened or closed by said controller means, said first valve being open at low or normal pressures and normally closed at high pressures;
   a second valve situated in said second fluid conduit and opened or closed by said controller means, said second valve being open at low or normal pressures and closed shortly after detection of high pressure;
   a bypass conduit connected to said first conduit for diverting fluid around said pump in said first conduit; and
   a third valve situated in said bypass conduit and opened or closed by said controller means, said third valve being closed at low or normal pressures and normally open at high pressures.

3. Apparatus as in claim 2 wherein said detecting and measuring means comprises a pressure transducer.

4. Apparatus as in claim 3 wherein said responsive means includes a pressure sensing averaging circuit in communication with said pressure transducer.

5. Apparatus as in claim 2 wherein said controller means also causes said valves to cycle between open and closed portions several times while high pressure persists and then to halt operation of all pumps and activate an alarm if said high pressure has not been reduced to normal pressure during said cycling.

6. Apparatus as in claim 1 wherein said responsive means comprises:
   motor and motor drive means for each of said pump, and
   controller means operatively connected to said pumps and responsive to signals from said pressure transducer to operate each pump through said motor and motor drive means independently as determined by whether said pressure is high, normal or low, said controller means causing said pumps to produce forward flow at low and normal pressure and to halt or reverse flow in at least the pump in the first of said fluid conduits at high pressure.

7. Apparatus as in claim 6 wherein said controller means also causes said pumps to cycle between forward and reverse flow if high pressure persists and to switch said pump to aspiration and activate an alarm if after several such cycles such high pressure has not been reduced to normal pressure during said cycles.

8. Apparatus as in claim 6 wherein said detecting and measuring means comprises a pressure transducer.

9. Apparatus as in claim 8 wherein said responsive means includes a pressure sensing averaging circuit in communication with said pressure transducer.

10. Apparatus as in claim 6 wherein said controller means responds to said transducer through an averaging circuit.

11. Apparatus as in claim 1 wherein the terminal portion of each said first and second fluid conduits distal to said source reservoir means are combined into a catheter.

12. Apparatus as in claim 11 where said catheter is a three-lumen catheter comprising a first lumen for passing fluid from a source reservoir to said organ or cavity, a second lumen for passing said fluid from said organ or cavity to a receiver reservoir and a third lumen for communicating said pressure to said measuring means.

13. A method for removing a soluble obstruction in a bodily organ or cavity, comprising:
   inserting a catheter into said organ or cavity, said catheter having at least two fluid conduits each communicating with source and receiver reservoir means for containing a fluid suitable for dissolving said obstruction, said catheter, reservoir means and conduits forming a fluid circuit;
   providing a pump in each of said conduits for moving said fluid through said conduits between said reservoir and said organ or cavity;
   detecting and measuring fluid pressure in said organ or cavity, said pressure being classified as high, normal or low according to predetermined physiological criteria;

causing said pumps by means responsive to said high, normal or low pressure to produce forward fluid flow in said circuit when said pressure is low or normal and to halt or reverse said fluid flow when said pressure is high, said fluid thus at normal or low pressure contacting and dissolving said obstruction.

14. A method as in claim 13 wherein said fluid is in turbulent flow while in contact with said obstruction.

15. A method as in claim 13 further comprising cycling said fluid flow between forward and reversed flow several times while said high pressure persists.

16. A method as in claim 15 further comprising halting said fluid flow and activating an alarm if said high pressure has not been reduced to normal pressure during said several cycles.

17. A method as in claim 13 wherein said bodily organ is a gallbladder and said obstruction is a gallstone.

18. Apparatus for removal of gallstones from the gallbladder, comprising:
  a reservoir for containing fluid capable of dissolving gallstones;
  first and second fluid conduits each having one end communicating with said reservoir and another end communicating with the gallbladder;
  pump means comprising first and second pumps operatively associated respectively with said first and second conduits for moving said fluid in said first conduit in the infusion direction from said reservoir into the gallbladder, and for moving said fluid in said second conduit in the aspiration direction from the gallbladder to said reservoir;
  whereby, by simultaneous infusion and aspiration, continuous withdrawal of said fluid after exposure to said gallstones can be maintained at a substantial rate over prolonged periods;
  said apparatus including a control system for selectively inhibiting infusion, said control system including means for continuously monitoring pressure within said gallbladder, means for determining the relationship of said pressure with respect to a desired range based on predetermined physiological criteria, and means for selectively inhibiting infusion in response to said pressure being above said desired range.

19. The apparatus of claim 18 wherein said control system includes means for inhibiting aspiration in response to said pressure being below said desired range.

20. In a gallstone removal apparatus which includes a liquid transfer system for introducing liquid solvent to and removing said liquid solvent from the gallbladder of a living patient via a catheter in a manner to cause the gallstone to disintegrate and be removed with the liquid;
  the improvement wherein the liquid transfer system includes a control system comprising a controller and means for continuously determining and supplying to the controller the actual liquid pressure within the gallbladder during the treatment;
  said controller having means to receive from the attending operator a pressure setting related to the predetermined pressure at which flow of the solvent out of the gallbladder into other parts of the body may occur and said controller being responsive to actual sensed gallbladder pressure to cause pump means to automatically reduce the quantity of solvent within said gallbladder upon the occurrence of actual gallbladder pressure in excess of a high pressure value based upon said setting, thereby preventing release of said solvent into the body.

21. The apparatus of claim 20 wherein said pump means comprises an infusion pump and an aspiration pump, said pumps capable of operating simultaneously to infuse and aspirate said solvent relative to said gallbladder through respective lumens of said catheter whereby continuous flow of said solvent into and out of said gallbladder can be maintained by said controller during normal operation, said controller adapted to stop infusion and continue aspiration when actual gallbladder pressure exceeds said high pressure value.

22. The apparatus of claim 21 wherein said controller is capable of operating said pump means to simultaneously infuse and aspirate over a set pressure range and in response to actual gallbladder pressure below said range, said controller adapted to automatically stop aspiration while maintaining infusion flow.

23. The apparatus of claim 18, 20 or 21 wherein the pump means is adapted to transfer the solvent into the gallbladder at rates in the range between about 50 ml/min to 300 ml/min.

24. The apparatus of claims 18, 20 or 21 programmed to respond to occurrence of a selected irregular pressure condition in said gallbladder by automatically momentarily reversing flow to clear a possible obstruction to normal flow.

25. The apparatus of claim 18, 20 or 21 wherein said control system includes averaging means that functions to prevent response to a transient high pressure signal such as coughing or laughing.

26. The apparatus of claim 18, 20 or 21 wherein said pump means is of the peristaltic type.

27. The apparatus of claim 18, 20 or 21 in combination with a multilumen catheter constructed to infuse and aspirate solvent with respect to said gallbladder, an independent lumen of said catheter adapted to transmit an actual pressure signal from said gallbladder to said control system.

28. The apparatus of claim 27 wherein said catheter is of curved configuration and the opening for said pressure transmitting lumen is on the inside surface of said curved configuration.

29. The apparatus of claim 18, 20 or 21 in which said pump means is provided with a controllable motor and said control system controls said flow by controlling the direction and speed of the motor.

30. The apparatus of claim 29 wherein said pump means comprises an infusion pump and an aspiration pump, each driven by a respective motor controlled by said control system.

31. The apparatus of claim 29 wherein said control system includes a microprocessor.

32. The apparatus of claim 18, 20 or 21 wherein a critical leakage pressure which differs from patient to patient is predetermined and the control system is adapted to conduct said infusion and aspiration in the manner preventing exceeding said pressure while solvent is within the gallbladder.

33. The apparatus of claim 32 including means for causing maximal aspiration upon the occurrence of actual gallbladder pressure of a value related to but below the predetermined critical pressure.

34. In a method of removing gallstones from the gallbladder of a patient by infusion and aspiration of a solvent, the steps of inputting into a control system a predetermined pressure value for the respective patient representing the pressure at which leakage from the gallbladder into other parts of the body may occur, infusing and aspirating the solvent into and out of the gallbladder, monitoring the actual fluid pressure within the gallbladder and, with said control system, in response to actual pressure approaching said predetermined value, stopping the infusion and aspirating solvent from the patient.

35. The method of claim 34 in which said predetermined value is related to the pressure in the gallbladder during normal contraction of the gallbladder that releases bile to the duodenum.

* * * * *